United States Patent [19]

Pike

[11] Patent Number: 4,539,849
[45] Date of Patent: Sep. 10, 1985

[54] TRANSDUCER ASSEMBLY INCLUDING A DISPOSABLE DOME

[75] Inventor: Kelly Pike, Santa Ana, Calif.

[73] Assignee: American Hospital Supply Corporation, Evanston, Ill.

[21] Appl. No.: 532,684

[22] Filed: Sep. 16, 1983

[51] Int. Cl.³ .............................................. G01L 7/08
[52] U.S. Cl. ....................................... 73/715; 73/756; 128/675
[58] Field of Search .................. 73/756, 741, 715; 128/675; 99/343, 342

[56] References Cited

U.S. PATENT DOCUMENTS

| | | |
|---|---|---|
| 190,651 | 5/1877 | Webster . |
| 344,312 | 6/1886 | Guillemin . |
| 1,286,819 | 12/1918 | Snyder . |
| 1,325,902 | 12/1919 | Novick . |
| 2,169,371 | 9/1936 | Payne ................................. 128/221 |
| 3,451,391 | 3/1963 | Tavel ................................... 128/36 |
| 3,499,434 | 3/1970 | Ullrich ................................ 128/673 |
| 4,063,553 | 12/1977 | Karsh ............................... 128/214 F |
| 4,072,056 | 2/1978 | Lee ..................................... 73/706 |
| 4,170,993 | 10/1979 | Alvarez ............................ 128/214 R |
| 4,185,641 | 1/1980 | Minior et al. ....................... 128/675 |
| 4,252,126 | 2/1981 | Mandl ................................ 128/673 |

Primary Examiner—Donald O. Woodiel
Attorney, Agent, or Firm—Gordon L. Peterson

[57] ABSTRACT

A transducer assembly comprising a transducer housing, a retainer mounted on the housing for generally axial movement relative to the housing and a collar for relatively moving the retainer and the housing along the path between a locking position and a releasing position. The transducer assembly also includes a dome which is coupled to the housing by cooperating lugs and retaining flanges on the dome and the retainer, respectively.

16 Claims, 5 Drawing Figures

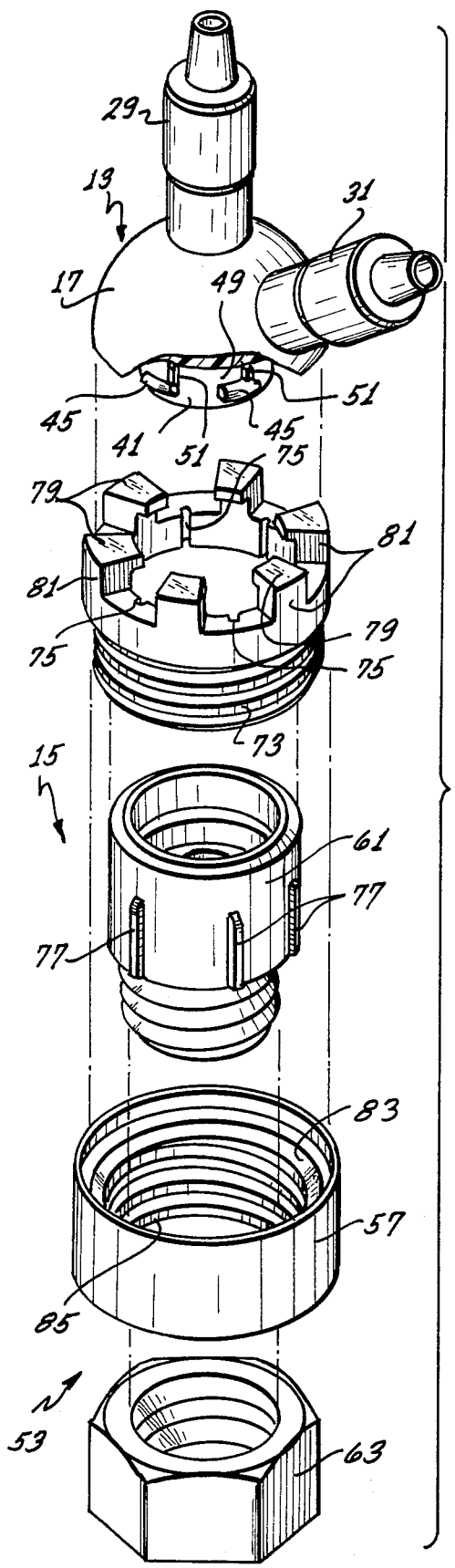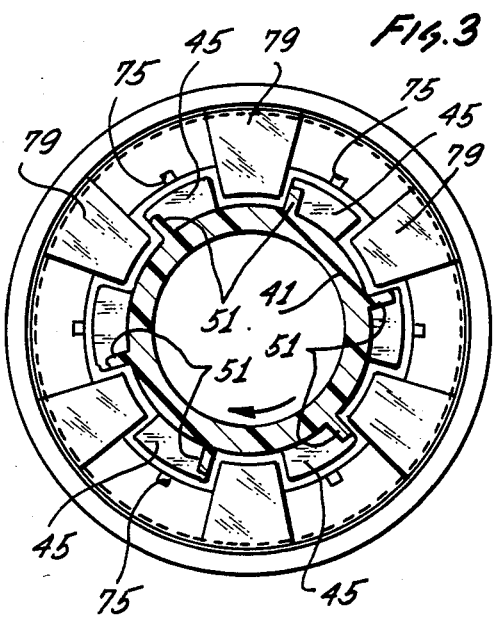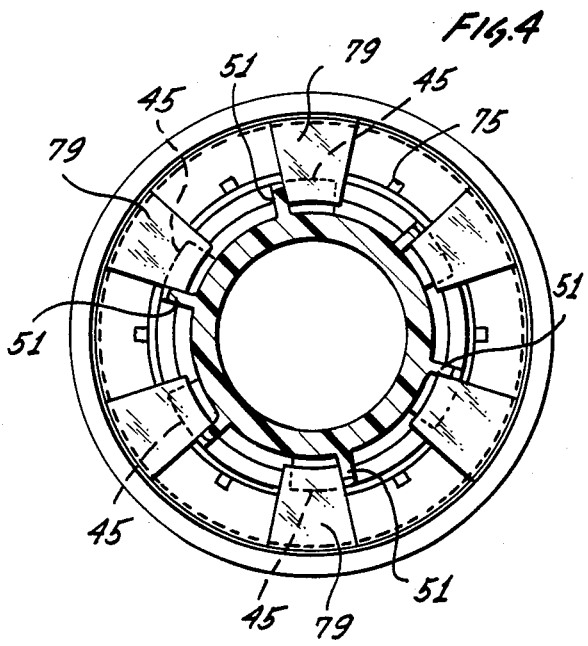

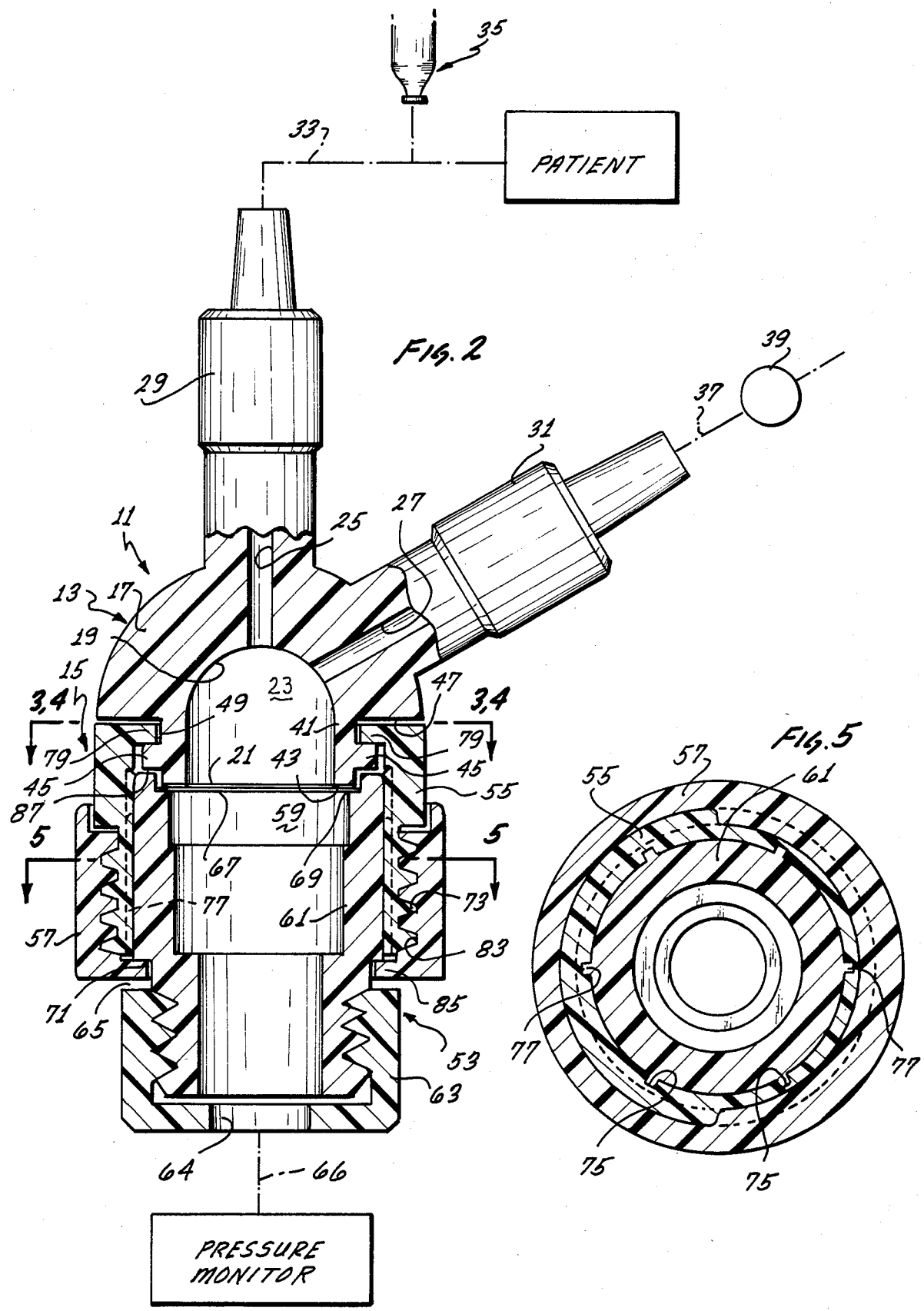

TRANSDUCER ASSEMBLY INCLUDING A DISPOSABLE DOME

BACKGROUND OF THE INVENTION

The blood pressure of a patient can be monitored by direct coupling of the patient's circulatory system to a pressure transducer assembly. In this event, the patient's blood, or a fluid in direct contact with the patient's blood, is provided to the transducer assembly. The transducer assembly converts the pressure of the blood to an electrical signal related to the blood pressure, and this signal can be appropriately displayed or recorded by a monitor.

A transducer assembly includes two primary components, i.e., a dome and a transducer. The dome is coupled to tubing, such as IV tubing, which may lead to the patient and elsewhere. The interior of the dome is in communication with the circulatory system of the patient and is a disposable component which is typically thrown away periodically along with any associated IV system. The transducer is a permanent part of the system which senses the pressure of the fluid received by the dome and converts it to a related electrical signal.

Because the dome is disposable, domes must be attached to, and detached from, the transducer many times. Accordingly, it is important that the coupling between the dome and transducer be easily locked and released without disturbing the tubing or the sensing portion of the transducer. One technique for attaching the dome to the transducer, which is illustrated in Minior et al U.S. Pat. No. 4,185,641 involves relative rotation between the dome and the transducer. Rotation of the dome twists the tubing coupled to it so that the attending technicians may have difficulty in determining where each tube runs. Turning the transducer, on the other hand, twists the electrical cords coupled to the transducer and can cause early failure of the cords.

Another prior art connection between the dome and transducer, which is illustrated by way of example in Lee U.S. Pat. No. 4,072,056 employs a bezel which must be rotated relative to both the dome and the transducer. It is difficult for the attending technician to hold the dome and transducer stationary while turning the bezel.

SUMMARY OF THE INVENTION

This invention provides a dome and transducer assembly which overcome the problems noted above with the prior art. With this invention, the dome can be attached to the transducer without rotating either the dome or the transducer. All that is required to obtain attachment is the rotation of an actuator, and this can be accomplished without rotating the dome or the housing.

With the transducer assembly of this invention, a retainer is mounted on a transducer housing for movement along a generally axial path relative to the housing. Actuating means relatively moves the retainer and the housing along the path between a locking position and a releasing position. This relative axial movement is used in coupling the dome to the transducer housing. For this purpose, coupling means is provided at least partially on the dome and the retainer, and they are responsive to the retainer being in the locking position for coupling the dome to the housing.

The actuating means can advantageously take the form of a rotatable collar threadedly coupled to the retainer and drivingly engageable with the housing so that rotation of the collar relatively moves the retainer and the housing axially. Although the collar is rotatable, coupling of the dome to the transducer housing is accomplished as a result of the relative axial movement between the dome and the housing.

In a preferred construction, the coupling means includes a plurality of circumferentially spaced lugs on the dome extending generally radially outwardly and a plurality of circumferentially spaced retaining flanges on the retainer extending generally radially inwardly and adapted to engage the lugs in the locking position. The coupling means also preferably includes bearing surfaces on the housing and the dome. With the above-described construction, the dome and the actuating means forcibly bear against axially spaced regions of the housing in the locking position.

The transducer includes a sensitive sensing portion or means, such as a strain gage, for sensing the pressure of the fluid in the dome. The sensing portion is located within the housing.

The dome preferably has a shoulder on its exterior spaced from the lugs to define a circumferentially extending groove which opens generally radially outwardly for receiving the retaining flanges. To control the relative angular orientation of the dome and the transducer, the dome may include at least one stop located adjacent one of the lugs. Preferably, such stop lies between the lug and the shoulder. In a preferred construction, the shoulder is annular and lies in a generally radial plane.

Although the features of this invention are particularly adapted for a transducer assembly, in a broader sense, this invention is also applicable to an assembly for making a measurement of a characteristic of a body fluid. In this event, the dome has a member at least partially defining the chamber for transmitting the characteristic of the body fluid to be measured out of the chamber, and means is provided at least partially within the housing for sensing the characteristic of the body fluid. In the case of a transducer assembly, the member is in the form of a flexible diaphragm that moves in response to pressure changes, and the sensing means includes an appropriate sensing portion, such as a strain gage for responding to the deflection of the diaphragm.

The invention, together with additional features and advantages thereof, may best be understood by reference to the following description taken in connection with the accompanying illustrative drawing.

BRIEF DESCRIPTION OF THE DRAWING

FIG. 1 is an exploded isometric view of a transducer assembly constructed in accordance with the teachings of this invention and with a portion of the dome broken away to expose two of the lugs and the associated stops.

FIG. 2 is a side elevational view partially in section of the transducer assembly and a schematic illustration of a system with which the transducer assembly may be used.

FIGS. 3 and 4 are sectional views taken along lines 3,4—3,4 of FIG. 2. In FIG. 3, the dome has an angular position in which each of the lugs is intermediate an adjacent pair of the retaining flanges, and in FIG. 4, the dome is rotated from the position of FIG. 3 so that the lugs are substantially beneath the associated retaining flanges.

FIG. 5 is a sectional view taken generally along line 5—5 of FIG. 2.

DESCRIPTION OF THE PREFERRED EMBODIMENT

FIGS. 1 and 2 show a transducer assembly 11 which generally comprises a dome 13 and a transducer 15. The dome 13 is a disposable element and includes a body 17 of plastic or other suitable material having a recess 19 therein which opens at the exterior of the body. A flexible diaphragm 21 is mounted on, and coupled to, the body 17 so that the diaphragm extends across the recess 19 to form a chamber 23 in the body.

The chamber 23 is completely sealed, except for ports 25 and 27 which extend through fittings 29 and 31, respectively, which are integral with the body 17. The chamber 23 is in direct communication with the circulatory system of a patient via the port 25 and a conduit 33 which may be, for example, in the form of IV tubing or a catheter. In the form shown in FIG. 2, the conduit 33 is IV tubing which forms a portion of a conventional IV set 35.

The port 27 vents the chamber 23 to the atmosphere through tubing 37 and a stop cock 39. The stop cock 39 is closed after the air has been expelled from the chamber 23.

In the embodiment illustrated, the body 17 has a generally dome-shaped or hemispherical outer surface, and this is useful so that any liquid falling on the body 17 tends to run harmlessly off of the dome. However, the body 17 need not have a dome-like or hemispherical configuration, and the word "dome" as used herein means that component which has a chamber for communicating with a body fluid, and that term does not connote or imply any geometrical limitations whatsoever.

The body 17 has an integral, annular boss 41 coaxial with the chamber 23 and terminating in an annular bearing surface 43 at the mouth of the recess 19. The diaphragm 21 is suitably bonded to the bearing surface 43.

A plurality of exposed, circumferentially spaced lugs 45 extends generally radially outwardly from the exterior of the boss 41. In the illustrated embodiment, there are six identical lugs 45, and they are spaced equally circumferentially as best seen in FIG. 3.

The body 17 has an annular shoulder 47 which, in the embodiment illustrated, lies in a generally radial plane. The shoulder 47 is spaced axially from the lugs 45 to define an intermittent circumferentially extending groove 49 which opens generally radially outwardly. The lugs 45 are axially intermediate the bearing surface 43 and the shoulder 47.

Six stops 51 are provided integrally with the boss 41. The stops 51 are optional, and if they are provided, various different constructions are possible. In the embodiment illustrated, each of the stops 51 is contiguous one end of an associated lug 45 (FIGS. 1 and 3), and the stops extend generally axially from the associated lug to the shoulder 47.

The transducer 15 comprises a housing 53, a retainer 55, actuating means in the form of a collar 57 and a sensing portion 59. Although the housing 53 can be of various different constructions, in the embodiment illustrated, it includes a tubular housing section 61 and a housing section 63 threaded onto the tubular housing section and forming an annular groove 65 therebetween. The housing section 63 has a central opening 64 through which electrical conductors 66 can extend to couple the transducer assembly 11 to suitable instrumentation, such as a conventional pressure monitor which converts the electrical signal into a suitable reading indicative of the pressure of the patient's blood.

The housing 53, which may be constructed of a suitable plastic or other material, serves to house the sensing portion 59 of the transducer, and for that purpose, has a hollow interior, the inner end of which is sealed by a flexible membrane 67. More specifically, the housing has an internal annular shoulder 69 to which the flexible membrane 67, and the usual membrane supporting structure is attached. The shoulder 69 also forms one bearing surface of the housing 53. An external shoulder 71 on one side of the groove 65 forms a second bearing surface of the housing, and these bearing surfaces are axially spaced. The sensing portion 59 is located entirely between the shoulders or bearing surfaces 61 and 71.

The diaphragm 21 transmits a signal related to the characteristic of the body fluid which communicates with the chamber 23. The membrane 67 must also transmit that signal to the sensing portion 59, and the sensing portion 59 can be any conventional means which senses the signal. In the embodiment illustrated, pressure is the characteristic to be sensed, and the pressure is transmitted by flexing of the diaphragm 21 and the membrane 67. The sensing portion 59 may include strain gages or other devices which respond to the flexing of the membrane 67 to provide an electrical signal related to the pressure of the blood or other body fluid in the chamber 23.

The retainer 55 is a tubular member of plastic or other suitable material having external threads 73 and internal axial grooves 75 (FIGS. 1 and 5) for receiving axially extending splines 77 on the tubular housing section 61. Thus, the housing 53 and the retainer 55 are mounted for relative movement along a generally axial path.

The retainer 55 has a plurality of circumferentially spaced retaining flanges 79 extending generally radially inwardly. Each of the flanges 79 is integral with a raised block 81, and the blocks are similarly circumferentially spaced. Preferably, the number of the flanges 79 equals the number of the lugs 45. As shown in FIG. 3, the circumferential spacing between the flanges 79 is just sufficient to accommodate one of the lugs 45. Similarly, the circumferential spacing between adjacent lugs 45 is just sufficient to accommodate one of the flanges 79.

The collar 57 is in the form of an annular nut having internal threads 83 which receive, and cooperate with, the external threads 73. The collar 57 has an annular lip 85 which is engageable with the shoulder 71 of the housing 53. Consequently, rotation of the collar 57 relatively moves the housing 53 and the retainer 55 along an axial path as defined by the grooves 75 and the splines 77.

To couple the dome 13 to the transducer 15, the collar 57 is rotated to raise (as viewed in FIG. 2) the retainer 55. The dome 13 is then positioned on the housing 53 as shown in FIG. 3, with the lugs 45 intermediate adjacent flanges 79. Next, the dome 13 is rotated slightly with respect to the transducer 15 to bring the lugs 45 beneath the associated flanges 79 and the stops 51 into contact with the associated flanges 79 as shown in FIG. 4. The stops 51 mark the limit of rotation of the dome 13. This rotation of the dome is very slight and may be, for example, about thirty degrees. The collar 57 is then rotated to relatively axially move the retainer 55 and the housing 53 so as to draw the flanges 79 closer to the housing and bring the bearing surface 43 of the dome into engagement with the bearing surface 69 of the housing as shown in FIG. 2. In this position, the dome 13 is very tightly clamped to the housing 53 by the retainer 55. Neither the dome 13 nor the retainer 55 is rotated when the collar 57 is rotated, and so there is no danger of twisting or entangling the conduit 33 and the tubing 37 nor the conductors 66.

In the assembled condition, there is an axial gap 87 between the lugs 45 and the top of the housing 53. This assures that the bearing surfaces 43 and 69 will be in contact to bring the diaphragm 21 and the membrane 67 into contact.

With the transducer assembly 11 assembled, it can be used in a conventional manner to monitor the blood pressure of the patient. Briefly, the chamber 23 is in communication with the circulatory system of the patient and so the diaphragm 21 and the contiguous membrane 67 can flex in response to pressure changes. Flexure of the membrane 67 is sensed by the sensing portion 59 which provides an electrical signal to the pressure monitor which is related to the blood pressure of the patient. The pressure monitor responds to this signal to provide a display of the blood pressure.

To replace the dome 13, it is only necessary to counterrotate the collar 57 to tend to axially separate the flanges 79 and the shoulder 69 of the housing. This enables the dome 13 to be removed by simply counterrotating the dome through a small angle to the position of FIG. 3 and axially withdrawing it from the transducer 15.

Although an exemplary embodiment of the invention has been shown and described, many changes, modifications and substitutions may be made by one having ordinary skill in the art without necessarily departing from the spirit and scope of this invention.

I claim:

1. A dome for attachment to a pressure transducer, said dome comprising:
    a body having a recess therein which opens at the exterior of the body;
    a flexible diaphragm;
    means for mounting the diaphragm on the body with the diaphragm extending across the recess to form a chamber in the body;
    said body having port means for providing communication through said body between the chamber and the exterior of the body whereby fluid can be admitted to said chamber;
    a plurality of exposed, circumferentially spaced lugs extending generally radially outwardly from the exterior of the body for use in attaching the dome to the pressure transducer; and
    said body having a shoulder on the exterior of the body spaced from the lugs to define an intermittent circumferentially extending groove which opens generally radially.

2. A dome as defined in claim 1 including a stop on said body adjacent one of said lugs.

3. A dome as defined in claim 1 wherein said body has a bearing surface which is adapted to bear against the pressure transducer.

4. A dome as defined in claim 1 wherein said shoulder is annular and lies in a generally radial plane.

5. An assembly for making a measurement of a characteristic of a body fluid, said assembly comprising:
    a housing;
    a retainer;
    means for mounting the retainer on said housing for movement along a generally axial path relative to the housing;
    actuating means for relatively moving the retainer and the housing along said path between a locking position and a releasing position;
    a dome having a chamber therein, said dome including port means for providing communication between the chamber and the exterior of the dome whereby the body fluid can communicate with the chamber and a member at least partially defining said chamber for transmitting a signal related to the characteristic of the body fluid out of said chamber;
    coupling means at least partially on said dome and said retainer responsive to the retainer being in said locking position for coupling the dome to the housing, said coupling means being releasable when the retainer is in the releasing position; and
    means at least partially within said housing for sensing said signal which is related to said characteristic of the body fluid.

6. An assembly as defined in claim 5 wherein said actuating means includes a collar threadedly coupled to said retainer and drivingly engageable with the housing whereby rotation of the collar relatively moves the retainer and the housing along said path.

7. An assembly as defined in claim 6 wherein said housing includes first and second housing sections and means to releasably join said housing sections to define an annular groove therebetween, and said collar includes a section projecting radially inwardly into said groove whereby the collar is retained on said housing.

8. An assembly as defined in claim 5 wherein said mounting means includes splines and cooperating grooves on the housing and the retainer.

9. An assembly as defined in claim 8 wherein said dome and said actuating means forcibly bear against axially spaced regions of the housing in said locking position.

10. An assembly as defined in claim 5 wherein said coupling means includes a plurality of circumferentially spaced lugs on said dome extending generally radially outwardly and a plurality of circumferentially spaced retaining flanges on the retainer extending generally radially inwardly and adapted to engage the lugs in said locking position.

11. An assembly as defined in claim 10 including a stop on said dome adjacent one of said lugs and engageable by an associated one of said flanges.

12. An assembly as defined in claim 10 wherein said actuator means includes a collar threadedly coupled to the retainer and drivingly engageable with the housing whereby rotation of the collar relatively moves the retainer and housing along said path, said retainer is tubular and a portion of the retainer lies radially between said housing and said collar.

13. An assembly as defined in claim 5 wherein said member of said dome is a flexible diaphragm and said characteristic of the body fluid is pressure.

14. An assembly as defined in claim 13 wherein said coupling means includes a plurality of circumferentially spaced lugs on said dome extending generally radially outwardly and a plurality of circumferentially spaced retaining flanges on the retainer extending generally radially inwardly and adapted to engage the lugs in said locking position.

15. A dome for attachment to a pressure transducer, said dome comprising:

a body having a recess therein which opens at the exterior of the body;

a flexible diaphragm;

means for mounting the diaphragm on the body with the diaphragm extending across the recess to form a chamber in the body;

said body having port means for providing communication through said body between the chamber and the exterior of the body whereby fluid can be admitted to said chamber;

a plurality of exposed, circumferentially spaced lugs extending generally radially outwardly from the exterior of the body for use in attaching the dome to the pressure transducer;

said body having a shoulder on the exterior of the body spaced from the lugs to define a circumferentially extending groove which opens generally radially;

said shoulder being annular and lying in a generally radial plane; and a stop on said body between one of said lugs and the shoulder.

16. A dome for attachment to a pressure transducer, said dome comprising:

a body having a recess therein which opens at the exterior of the body;

a flexible diaphragm;

means for mounting the diaphragm on the body with the diaphragm extending across the recess to form a chamber in the body;

said body having port means for providing communication through said body between the chamber and the exterior of the body whereby fluid can be admitted to said chamber;

a plurality of exposed, circumferentially spaced lugs extending generally radially outwardly from the exterior of the body for use in attaching the dome to the pressure transducer;

said body having a bearing surface which is adapted to bear against the pressure transducer; and a stop on said body adjacent one of said lugs, said one lug being intermediate the stop and the bearing surface.

* * * * *

UNITED STATES PATENT OFFICE
CERTIFICATE OF CORRECTION

Patent No. 4,539,849  Dated September 10, 1985

Inventor(s) Kelly Pike

It is certified that error appears in the above-identified patent and that said Letters Patent are hereby corrected as shown below:

Claim 9, line 1 change "8" to -- 5 --.

Signed and Sealed this

Twenty-eighth Day of January 1986

[SEAL]

Attest:

DONALD J. QUIGG

Attesting Officer

Commissioner of Patents and Trademarks